United States Patent [19]

Lannert

[11] 4,182,684
[45] Jan. 8, 1980

[54] MACHINE DISHWASHING COMPOSITION
[75] Inventor: Kent P. Lannert, Freeburg, Ill.
[73] Assignee: Monsanto Company, St. Louis, Mo.
[21] Appl. No.: 961,594
[22] Filed: Nov. 17, 1978

Related U.S. Application Data

[60] Continuation of Ser. No. 830,249, Sep. 2, 1977, abandoned, which is a division of Ser. No. 670,336, Mar. 25, 1976, Pat. No. 4,118,420, which is a continuation of Ser. No. 471,088, May 17, 1974, abandoned.

[51] Int. Cl.² ............................................. C11D 7/54
[52] U.S. Cl. ..................................................... 252/99;
252/95; 252/132; 252/135; 252/535; 252/539;
252/DIG. 11; 252/174.19; 562/503;
562/505; 562/506; 562/508; 562/583
[58] Field of Search ................ 252/99, 95, 89 R, 132,
252/135, 535, 539, DIG. 11; 260/535 B

[56] References Cited
U.S. PATENT DOCUMENTS

| | | | |
|---|---|---|---|
| 3,742,045 | 6/1973 | Lannert | 252/135 X |
| 3,970,698 | 7/1976 | Lannert | 252/99 X |

Primary Examiner—Mayer Weinblatt
Attorney, Agent, or Firm—N. E. Willis; E. P. Grattan; F. D. Shearin

[57] ABSTRACT

A machine dishwashing composition is provided which comprises the following: (a) from 5 to 90 percent by weight of a compound corresponding to the formula

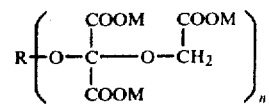

wherein M is alkali metal or ammonium and wherein n is a number from 1 through 3, and wherein R is selected from an alkyl radical having from 1 to 20 carbon atoms, an alkenyl radical having from 1 to 20 carbon atoms, an alkynyl radical having from 1 to 20 carbon atoms, a cycloalkane radical having from 3 to 20 carbon atoms, an alkanol radical having from 2 to 20 carbon atoms, an ether radical having at least 3 carbon atoms, an aryl radical having at least 6 carbon atoms, a substituted aryl radical having at least 6 carbon atoms wherein the substituents are halogen, nitro, amide or carboxyalkyl substituents, aralkyl radicals having at least 7 carbon atoms and arylether radicals having at least 7 carbon atoms, and (b) from 0 to 5 percent by weight of a low-foaming anionic or nonionic surfactant, (c) a chlorine-providing material in an amount sufficient to provide from 0.5 percent to 2 percent by weight available chlorine, and (d) from 5 percent to 30 percent by weight soluble sodium silicate having an $SiO_2$ to $Na_2O$ mole ratio of from 1:1 to 3.2:1.

6 Claims, No Drawings

MACHINE DISHWASHING COMPOSITION

This is a continuation of application Ser. No. 830,249, filed 9/2/77, now abandoned, which is a divisional of application Ser. No. 670,336, filed 3/25/76, now U.S. Pat. No. 4,118,420 issued Oct. 3, 1978, which is a continuation of application Ser. No. 471,088, filed May 17, 1974, and now abandoned.

BACKGROUND OF THE INVENTION

This invention relates to novel compounds useful as complexing agents for various metal and/or alkaline earth metal ions and to detergent formulations containing such compounds as functional ingredients.

It is well recognized that compounds having the ability to complex metal and/or alkaline earth metal ions which contribute to water "hardness", e.g. magnesium and calcium are useful in a variety of applications such as water treatment (e.g., softening, scale inhibition). (It is noted that some complexing agents also exhibit the ability of preventing precipitation of hardness ions from water even when used in quantities stoichiometrically insufficient to sequester the hardness ions. Such agents are said to exhibit "threshold" effect.) Additionally, some such compounds exhibit the ability to enhance, potentiate or supplement the cleaning ability of detergent formulations and are useful as functional ingredients thereof. Conventionally, such ingredients are referred to as detergency "builders" although in some applications, e.g., machine dishwashing formulations, the functionality of such compounds appears to be more than or different from a mere "building" of the performance of other ingredients of the formulation.

The provision of novel complexing agents has long been a continuing objective of those skilled in the art in view of the varied, recognized utilities of such materials.

SUMMARY OF THE INVENTION

It is an object of this invention to provide novel compounds useful as complexing agents for various metal and/or alkaline earth metal ions -particularly ions such as magnesium and calcium- and which are useful as functional ingredients in detergent formulations and/or exhibit surface active properties.

The compounds of the invention are characterized by the presence of at least one

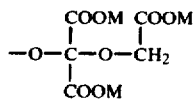

substituent (M, being alkali metal or ammonium). These compounds, their preparation and use will be understood from the following description of the preferred embodiments.

DESCRIPTION OF THE PREFERRED EMBODIMENTS

The compounds of the present invention correspond to alcohols having an active alcoholic hydroxy group replaced with a substituent represented by the formula

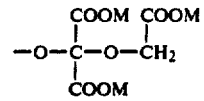

wherein M is alkali metal or ammonium and acids and esters thereof, provided, that the moiety to which the

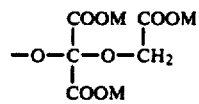

substituent is attached is other than

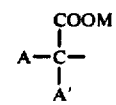

wherein A and A' are hydrogen or methyl.

The term "active alcoholic hydroxy group" is used to denote an alcoholic hydroxy group convertable to a conjugate base group reactive with diethyl ketomalonate to form a substituent represented by the formula

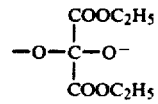

(The —O⁻ will, of course be associated with the cation of the conjugate base, e.g. —O⁻Na⁺)

The conversion of alcohols to their conjugate base forms is well understood. The conjugate base is obtained by reacting the alcohol with a base sufficiently strong to deprotonate a hydroxy group. Generally, deprotonization of reactive hydroxy groups is readily accomplished with sodium, potassium, sodium hydride, potassium hydride, sodium or potassium t-butoxide, sodium or potassium amide, etc. The reaction is conveniently conducted at temperatures of the order of 0° C. to 115° C. in any solvent for the alcohol which is not adversely reactive with the strong base. Examples of solvents suitable for use with various alcohols include, tetrahydrofuran, dimethylsulfoxide, dimethylformamide, ethylether, 1,2-dimethoxyethane, bis(2-methoxyethyl)ether, or the like. In those instances where the reactant alcohol is a liquid, an excess of such alcohol may be employed as the solvent. Mixed solvents can be used, if desired. More detailed discussion of the conversion of alcohols to conjugate bases is found in such references as Morrison and Boyd, *Organic Chemistry*, 3rd edition, Allyn and Bacon, Inc. (1973) pp. 526, 527; Feuer and Hooz, *The Chemistry of the Ether Linkage*, edited by Patai, Interscience Publishers (1967), Chapter 10, p. 447; and Schmidt and Bayer, *Methoden Der Organischen Chemie* (Houben-Weyl) Band VI/2, Georg Theime Verlag, (1963) Saurstoff Vergindunger 1, Teil 2 and bibliographies provided in the foregoing references.

The conjugate base form of the alcohol is then reacted with anhydrous diethylketomalonate, preferably at temperatures of from —50° to 60° C. and preferably in the solvent used for preparation of the conjugate base. The occurrence of the reaction is readily detected by conventional analytical techniques e.g. hydrogen or carbon 13 nuclear magnetic resonance spectral shifts or by observance of the disappearance of the characteristic yellow to yellow-green color of anhydrous diethylketomalonate.

When polydroxy alcohols are reacted as above resulting

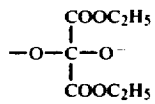

substituents may undergo transesterification with other sterically accessible hydroxy groups of the alcohol to form a cyclic lactone containing a

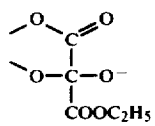

moiety. Thus, when an alcohol is tested in reactions as described above to determine if all or some of its hydroxy groups are "active" the formation of either a

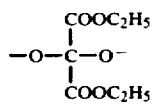

substituent or a lactone containing a

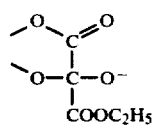

moiety confirms the presence of an active hydroxy group.

By way of further description, the compounds of this invention can be represented by the formula

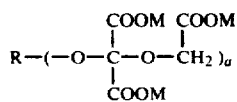

in which R is an organic radical corresponding to the residue of an alcohol having at least one active alcoholic hydroxy group removed therefrom and a is an integer equal to the number of hydroxy groups removed from the corresponding alcohol.

Although the compounds of this invention are described above by reference to analogous alcohols and are, as hereinafter explained, preferably derived from alcohols, no intention to limit the compounds of this invention to those actually derived from alcohols should be implied. In fact, the compounds of this invention can be prepared by synthetic techniques not requiring active hydroxy containing compounds as precursors. Therefore, this mode of description is merely intended to facilitate an understanding of the scope of the invention.

Examples of the compounds of this invention include substituted:

(a) alkanes such as

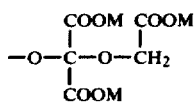

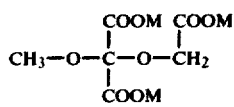

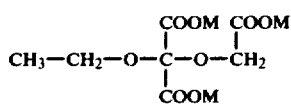

(The above two compounds are particularly preferred embodiments of the invention in view of excellent performance as detergency builders. It is further noted that these compounds are readily biodegradable which is quite unexpected in view of the resistance to biodegradability of a carboxylated analog,

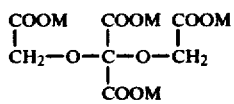

which analog is disclosed in U.S. Pat. No. 3,742,045.)

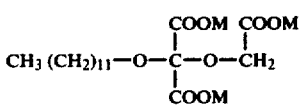

(Substituted long chain alkanes, e.g. $C_{10}$ to $C_{20}$, of this type exhibit surface active properties as well as complexing properties and are, therefore, additionally useful as emulsifiers, foaming agents, etc.);

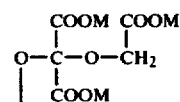

CH$_3$—CH$_2$—CH$_2$—CH$_2$—CH—CH$_2$—CH$_3$ ;

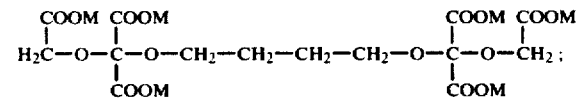

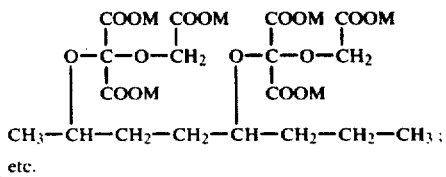

etc.

(b) cycloalkanes such as

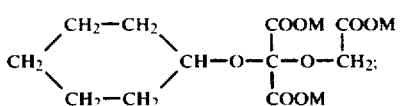

-continued

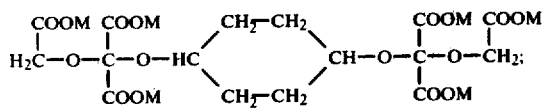

(c) alkanols such as

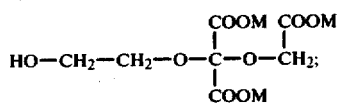

(d) ethers such as

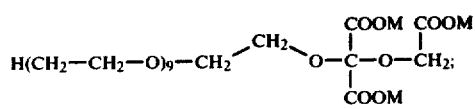

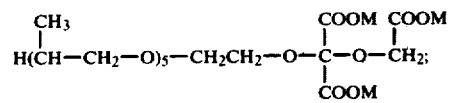

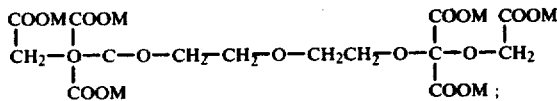
etc.

(e) aromatics such as

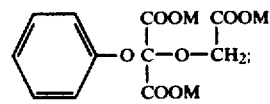

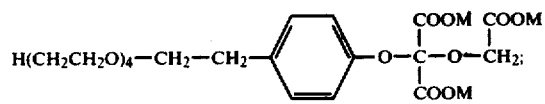

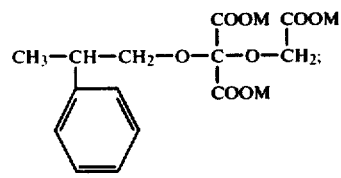

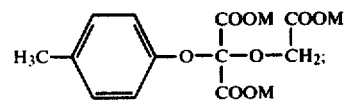

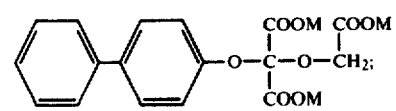
etc.

The moieties to which the

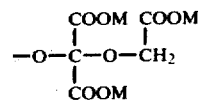

substituents are attached may bear other substituents which are not chemically incompatible with the

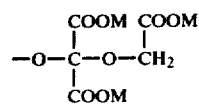

moiety.

For convenience, the compounds of this invention have been exemplified above in the salt forms; however, the corresponding ester and acid forms will be apparent to those skilled in the art. It is pointed out that in some instances, for example in the case of a compound such as

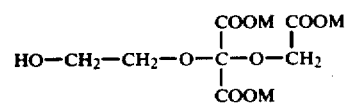

the corresponding ester and acid forms may exhibit a lactone structure such as

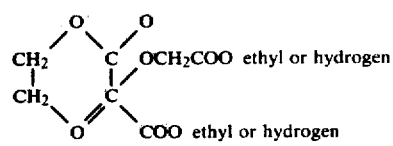

The compounds of this invention are most conveniently prepared by reacting an alcohol containing an active alcoholic hydroxy group with a strong base to form the conjugate base form for the alcohol. Such reactions have previously been described in the discussion of the definition of "active alcoholic hydroxy groups". In general, the use of sodium or potassium metals or hydrides to convert —OH groups to —O$^-$Na$^+$ or —O$^-$K$^+$ groups is preferred in the case of alcohols sufficiently acidic to react with these bases.

The conjugate base form of the alcohol is then reacted with a ketomalonate ester

which will convert the —O$^-$ substituent to a

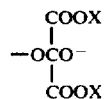

substituent, or may, if for example the —O$^-$ substituent is attached to a carbon atom adjacent to an hydroxy substituted carbon atom form a lactone containing the moiety.

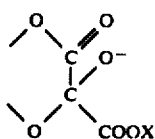

In the above formulae, X may be any organic moiety which will not, by virtue of chemical reactivity or stearic hindrance, interfere with the reaction. The reaction will proceed in all cases wherein X is a lower alkyl such as methyl or ethyl. However, it is generally desirable, where permissible from the standpoint of chemical reactivity and stearic hindrance, that X correspond to the organic moiety to which the conjugate base form of the alcoholic hydroxy group is attached in order to prevent formation of a mixture of products via transesterification reactions and the difficulties attendant to separation of such mixtures.

The reaction with the ketomalonate ester is preferably conducted in the same solvent system used in converting the alcohol to its conjugate base at temperatures from −50° to 60° C., preferably from −20° to 30° C. Alternatively, the alcohol can first be reacted with the ketomalonate ester followed by reaction with strong base to form the

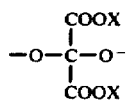

or

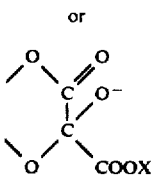

containing product. Generally, however, conversion of the alcohol to its conjugate base form followed by reaction with the ester is preferred.

When the starting alcohol contains more than one active hydroxy group, the quantities of reactants and severity of reaction conditions employed in the foregoing reaction will determine whether only one or more of such groups are replaced in the reactions.

The

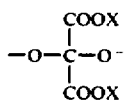

or

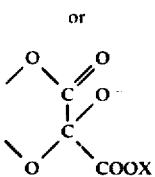

containing product is then reacted with bromo or iodo acetate $ZCH_2COOX$ (Z is Br or I) to convert to —O⁻ substituent to a —OCH$_2$COOX substituent thereby yielding the ester form of the compounds of the invention.

The bromoacetate or iodoacetate may be added as such or produced in situ, e.g., by using a mixture of sodium iodide and chloroacetate. Reaction temperatures are not critical, a temperature range of −20° to 100° C. usually being satisfactory.

In general, the reactions described can be conducted at atmospheric pressure, although, in some instances, it may be desirable to provide reflux means or pressure to prevent excessive loss of reactants or solvents, or to permit use of higher temperatures.

Reaction of the esters with alkali metal hydroxide yields the alkali metal salt forms of the compounds of the invention which can be converted to the acid form by acidulation (for example, by means of a strong acid ion exchange resin such as sulfonated polystyrene or a strong mineral acid.

Reaction of the acid form with ammonium hydroxide will yield the ammonium salt forms of the compounds of this invention.

As discussed above, the acid and ester forms of the compounds of this invention are useful as intermediates for preparation of the salt forms. The

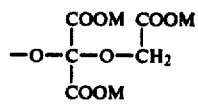

substituents of the compounds of this invention provide sequestrant and detergency builder functionality. Other useful functionality may be provided by the moiety to which the

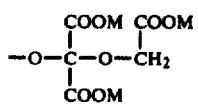

substituents are attached.

As seen from the foregoing discussion, the moieties to which

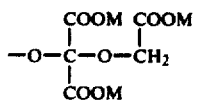

substituents may be attached include aliphatic, alicyclic, aromatic, alkyl aromatic, alcohol, and ether moieties.

Preferred classes of the compounds of this invention are those in which the moiety to which the

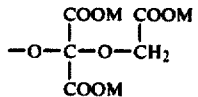

substituents are attached are:

(1) an alkane containing 1 to 20 carbon atoms. Substituted $C_1$ to $C_4$ alkanes provide particularly effective builder functionality whereas the higher alkanes additionally provide surfactant functionality.

(2) polyalkylene oxides particularly polyethylene oxides containing 2 to 20 molecular proportions of ethylene oxide are effective solublizing agents having sequestrant properties.

(3) alkyl benzenes (preferably having alkyl chains containing 5 to 20, most preferably 8 to 15 carbon atoms) are surfactants having sequestering properties. Compounds wherein the

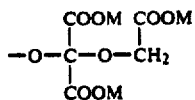

substituent is attached to the benzene ring are particularly preferred.

In general, compounds in which the

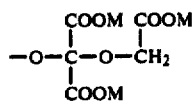

substituents constitute at least 50%, preferably at least 85% of the weight of the compound are preferred for applications wherein sequestrant or builder functionality is of primary importance. It is further generally preferred that such substituents be attached to uncarboxylated carbon atoms. Generally, compounds having one or two of such substituents are preferred from the standpoint of ease of synthesis.

In detergency builder applications, the use of the alkali metal salts, particularly the sodium salt is preferred. However, in some formulations (such as liquid formulations where greater builder solubility is required) the use of ammonium or alkanol ammonium salts may be desirable.

The detergent formulations will contain at least 1% by weight and preferably at least 5% by weight of the salt forms of compounds of this invention. In order to obtain the maximum advantages of the builder compositions of this invention, the use of from 5% to 75% of these salts is particularly preferred. The salt compounds of this invention can be the sole detergency builder or these compounds can be utilized in combination with other detergency builders which may constitute from 0 to 95% by weight of the total builders in the formulation. By way of example, builders which can be employed in combination with the novel salt compounds of this invention include water soluble inorganic builder salts such as alkali metal polyphosphates, i.e., the tripolyphosphates and pyrophosphates, alkali metal carbonates, borates, bicarbonates and silicates and water soluble organic builders including amino polycarboxylic acids and salts such as alkali metal nitrilotriacetates, cycloalkane polycarboxylic acids and salts, ether polycarboxylates, alkyl polycarboxylates, epoxy polycarboxylates, tetrahydrofuran polycarboxylates such as 1,2,3,4 or 2,2,5,5 tetrahydrofuran tetracarboxylates, benzene polycarboxylates, oxidized starches, amino (trimethylene phosphonic acid) and its salts, diphosphonic acids and salts (e.g. methylene diphosphonic acid; 1-hydroxy ethylidene diphosphonic acid) and the like.

The detergent formulations will generally contain from 5% to 95% by weight total builder (although greater or lesser quantities may be employed if desired) which, as indicated above, may be solely the builder salt compounds of this invention or mixtures of such compounds with other builders. The total amount of builder employed will be dependent on the intended use of the detergent formulation, other ingredients of the formulation, pH conditions and the like. For example, general laundry powder formulations will usually contain 20% to 60% builder; liquid dishwashing formulations 11% to 12% builder; machine dishwashing formulations 60% to 90% builder. Optimum levels of builder content as well as optimum mixtures of builders of this invention with other builders for various uses can be determined by routine tests in accordance with conventional detergent formulation practice.

The detergent formulations will generally contain a water soluble detergent surfactant although the surfactant ingredient may be omitted from machine dishwashing formulations. Any water soluble anionic, nonionic, zwitterionic or amphoteric surfactant can be employed.

Examples of suitable anionic surfactants include soaps such as the salts of fatty acids containing about 9 to 20 carbon atoms, e.g. salts of fatty acids derived from coconut oil and tallow; alkyl benzene sulfonates—particularly linear alkyl benzene sulfonates in which the alkyl group contains from 10 to 16 carbon atoms; alcohol sulfates; ethoxylated alcohol sulfates; hydroxy alkyl sulfonates; alkenyl and alkyl sulfates and sulfonates; monoglyceride sulfates; acid condensates of fatty acid chlorides with hydroxy alkyl sulfonates and the like.

Examples of suitable nonionic surfactants include alkylene oxide (e.g., ethylene oxide) condensates of mono and polyhydroxy alcohols, alkyl phenols, fatty acid amides, and fatty amines; amine oxides; sugar derivatives such as sucrose monopalmitate; long chain tertiary phosphine oxides; dialkyl sulfoxides; fatty acid amides, (e.g., mono or diethanol amides of fatty acids containing 10 to 18 carbon atoms), and the like.

Examples of suitable zwitterionic surfactants include derivatives of aliphatic quaternary ammonium compounds such as 3-(N,N-dimethyl-N-hexadecyl ammonio) propane-1-sulfonate and 3-(N,N-dimethyl-N-hexadecyl ammonio)-2-hydroxy propane-1-sulfonate.

Examples of suitable amphoteric surfactants include betains, sulfobetains and fatty acid imidazole carboxylates and sulfonates.

It will be understood that the above examples of surfactants are by no means comprehensive and that numerous other surfactants are known to those skilled in the art. It will be further understood that the choice and use of surfactants will be in accordance with well understood practices of detergent formulation. For example, anionic surfactants, particularly linear alkyl benzene sulfonate are preferred for use in general laundry formulations, whereas low foaming nonionic surfactants are preferred for use in machine dishwashing formulations.

The quantity of surfactant employed in the detergent formulations will depend on the surfactant chosen and the end use of the formulation. In general, the formulations will contain from 5% to 50% surfactant by weight, although as much as 95% or more surfactant may be employed if desired. For example, general laundry powder formulations normally contain 5% to 50%, preferably 15% to 25% surfactant; machine dishwashing formulations. 0.5% to 5%; liquid dishwashing formulations 20% to 45%. The weight ratio of surfactant to builder will generally be in the range of from 1:12 to 2:1.

In addition to builder and surfactant components, detergent formulations may contain fillers such as sodium sulfate and minor amounts of bleaches, dyes, optical brightners, soil anti-redeposition agents, perfumes and the like.

In machine dishwashing compositions the surfactant will be a low-foaming anionic or preferably, nonionic surfactant which will constitute 0 to 5% of the formulation.

The term "low-foaming" surfactant connotes a surfactant which, in the foaming test described below, reduces the revolutions of the washer jet-spray arm during the wash and rinse cycles less than 15%, preferably less than 10%.

In the foaming test, 1.5 grams of surfactant is added to a 1969 Kitchen-Aid Home Dishwasher, Model No. KOS-16, manufactured by Hobart Manufacturing Company which is provided with means for counting revolutions of the washer jet-spray arm during wash and rinse cycles. The machine is operated using distilled water feed at a machine entrance temperature of 40° C. The number of revolutions of the jet-spray arm during the wash and rinse cycles is counted. The results are compared with those obtained by operation of the machine using no surfactant charge and the percentage decrease in the number of revolutions is determined.

The surfactant should, of course, be compatible with the chlorine containing component hereinafter discussed. Examples of suitable nonionic surfactants include ethoxylated alkyl phenols, ethoxylated alcohols (both mono- and di- hydroxy alcohols), polyoxyalkylene glycols, aliphatic polyethers and the like. The widely commercially utilized condensates of polyoxypropylene glycols having molecular weights of from about 1400 to 2200 with ethylene oxide (the ethylene oxide constituting 5 to 35 weight percent of the condensate) are, for example, advantageously used in the machine dishwashing formulations of this invention.

Suitable low-foaming anionic surfactants include alkyl diphenyl ether sulfonates such as sodium dodecyl diphenyl ether disulfonates and alkyl naphthalene sulfonates.

Mixtures of suitable low-foaming surfactants can be utilized if desired.

In addition, machine dishwashing formulations will contain sufficient chlorine providing compound to provide 0.5% to 2% available chlorine. For example, the formulation may contain from 0.5% to 5%, preferably 1% to 3% of a chlorocyanurate or from 10% to 30% chlorinated trisodium phosphate. Suitable chlorocyanurates are sodium and potassium dichlorocyanurate; [(monotrichloro) tetra-(monopotassium dichloro)] penta-isocyanurate; (monotrichloro) (monopotassium dichloro) diisocyanurate.

Machine dishwashing compositions should additionally contain from 5% to 30% soluble sodium silicate having an SiO₂ to Na₂O mole ratio of from 1:1 to 3.2:1 preferably about 2.4:1 to inhibit corrosion of metal parts of dishwashing machines and provide over-glaze protection to fine china.

Machine dishwashing compositions will generally contain at least 10%, preferably at least 20% builder, up to a maximum of about 90% builder. The new salt compounds of this invention should constitute at least 5% of the weight of the machine dishwashing formulation.

The invention is further illustrated by the following examples wherein all parts and percentages are by weight unless otherwise indicated.

EXAMPLE I

A slurry of 70 grams sodium hydride in 1500 ml. tetrahydrofuran is prepared and 125 ml. methanol is added, the temperature being maintained below 35° C. The mixture is stirred for about 1 hour at 25° to 30° C. and cooled to about 0° C. About 409 grams dimethyl ketomalonate is added, following which 444 grams methyl bromoacetate is added. The mixture is stirred for about 1 hour, the temperature being maintained below 10° C. The temperature is then slowly raised and the reaction mixture refluxed for 18 hours.

The tetrahydrofuran is evaporated and the residue dissolved in a mixture of water and ethyl ether. The mixture is allowed to separate and the product containing ether layer is removed and washed with water. The ether is dried over CaSO₄, evaporated and the residue vacuum distilled with trimethyl 2-(carboxymethoxy)-2-methoxymalonate

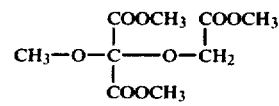

product being collected at 110° to 113° C./0.05 mm Hg. A solution of 466 grams of the above ester product in 466 grams methanol is added to 1000 grams of 25% sodium hydroxide aqueous solution. (After about ¼ of the ester solution has been added, the temperature is about 60° C. and 200 ml. water is added; ester addition is completed and 300 ml. water and 500 ml. methanol are added.)

The slurry is cooled to about 25° C. with stirring and filtered. The solid product is trisodium 2-(carboxymethoxy)-2-methoxymalonate.

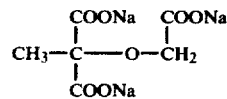

EXAMPLE II

A slurry of 41.6 grams sodium hydride in 1200 ml. tetrahydrofuran is prepared and 130 ml. ethanol added, the temperature being maintained below 30° C. The mixture is cooled to about 5° C. and maintained at that temperature for about 2 hours after which 400 grams diethyl ketomalonate is added, the temperature being maintained below 10° C. Ethyl bromoacetate (384 grams) is then added and the temperature maintained below 5° C. for 2 hours. The mixture is then warmed to 25° C. and maintained at about that temperature for 12 hours with stirring. The temperature is then raised to and maintained at 40° C. for 1 hour.

The tetrahydrofuran is evaporated and the residue dissolved in ether and washed with water. The ether fraction is separated and dried over calcium sulfate. The ether is evaporated and the product triethyl 2-(carboxymethoxy)-2-ethoxymalonate

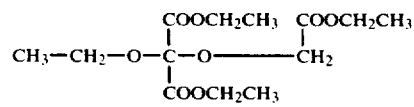

separated from the residue by distillation.

A solution of 547 grams of the above ester product in 200 ml. ethanol is added to 1020 grams 25% sodium hydroxide aqueous solution, the temperature being maintained below 45° C. The mixture becomes thick and 300 ml. ethanol is added to provide a stirrable slurry which is warmed to 45° C., cooled to 25° C. after 2 hours, and allowed to stand for 12 hours. Additional ethanol (100 ml.) is added and the slurry filtered to separate the solid trisodium 2-(carboxymethoxy)-2-ethoxymalonate

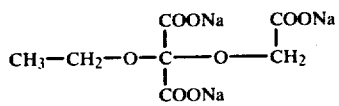

product.

EXAMPLE III

A solution of 58 grams dodecyl alcohol in 50 ml. dimethyl formamide is added, at 25° C., to a slurry of 7 grams sodium hydride in 500 ml. dimethyl formamide. The mixture is stirred at 25° C. for 1 hour and then at 40° C. for an additional hour.

The mixture is cooled to about −20° C. and 50 grams of diethyl ketomalonate is added. After several minutes stirring, 48 grams of ethyl bromoacetate is added, the temperature being maintained between −7° and −30° C. The reaction mixture is allowed to warm to 25° C. and is stirred for 12 hours.

The product ester triethyl 2-(carboxymethoxy)-2-dodecoxymalonate

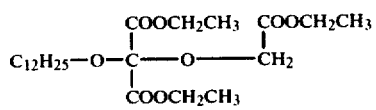

is separated by extraction with ethyl ether and purified by distillation.

About 75 grams of the above ester product in 50 ml. methanol is added to 125 grams of 25% sodium hydroxide aqueous solution cooled with an ice bath. An additional 100 ml. methanol is added and the resultant slurry is stirred for 1 hour at 25° C. The slurry is then filtered to separate solid trisodium 2-(carboxymethoxy)-2-dodecoxymalonate

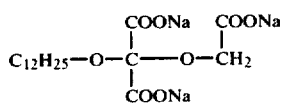

product.

EXAMPLE IV

Diethylene glycol (14 grams) is added to a slurry of about 6.4 grams sodium hydride in 300 ml. dimethyl formamide. The mixture is cooled to 0° C. and, stirred until reaction appears complete, and cooled to −50° C. About 50 grams diethyl ketomalonate is added followed by addition of 48 grams ethyl bromoacetate. The temperature is raised slowly to about −20° C. at which point foaming is observed. After foaming ceases, the temperature is raised to 25° C. the mixture is stirred for 12 hours.

The dimethyl formamide is evaporated and the product residue hexaethyl 4,4,12,12-tetracarboxy-3,5,8,11,13-pentaoxapentadecandioate

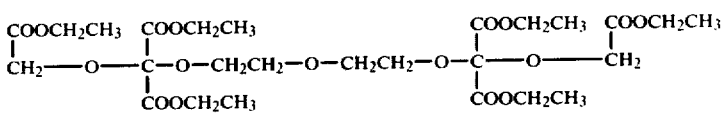

purified by washing with water and molecular distillation.

Reaction of the above ester with aqueous sodium hydroxide yields hexasodium 4,4,12,12-tetracarboxy-3,5,8,11,13-pentaoxapentadecandioate

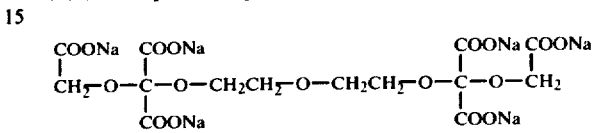

EXAMPLE V

A solution of 10 grams phenol in dimethyl formamide is added to a slurry of 24 grams sodium hydride in 500 ml. dimethyl formamide. Upon completion of reaction, the mixture is cooled to −20° C. and 174 grams diethyl ketomalonate is added followed by 167 grams ethyl bromoacetate.

The mixture is warmed to room temperature and stirred for two hours.

The ester product triethyl 2-(carboxymethoxy)-2-phenoxymalonate

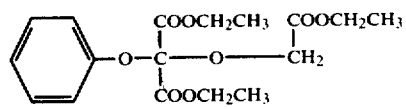

is converted to the salt trisodium 2-(carboxymethoxy)-2-phenoxymalonate

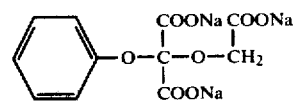

by reaction with aqueous sodium hydroxide.

EXAMPLE VI—XLIX

One mole of the active hydroxy containing compounds shown in Table I, below is slowly added to a slurry of 24 grams sodium hydride in dimethyl formamide or tetrahydrofuran solvent. The quantity of solvent is sufficient to render the reaction mixture stirrable and additional solvent is added during the reaction as required. One mole of diethyl ketomalonate is added while maintaining the temperature as low as consistent with reasonable reaction rate in order to minimize formation of by-products via transesterification.

One mole of ethyl bromoacetate is added and the temperature increased to about 70° C.

Upon completion of the reaction, the solvent is removed under reduced pressure and the product ester residue shown in Table I, below, is purified by conventional extraction and/or distillation techniques.

The ester is dissolved in ethanol and reacted with aqueous sodium hydroxide to yield the salt product shown in Table I.

TABLE I

| Example | Hydroxy Containing Compound | Ester Product (5) | Salt Product (5) |
|---|---|---|---|
| VI | C₂₀H₄₁OH | $C_{20}H_{41}-O-\overset{\overset{\displaystyle COOCH_2CH_3}{|}}{\underset{\underset{\displaystyle COOCH_2CH_3}{|}}{C}}-O-CH_2-COOCH_2CH_3$ | $C_{20}H_{41}-O-\overset{\overset{\displaystyle COONa}{|}}{\underset{\underset{\displaystyle COONa}{|}}{C}}-O-CH_2-COONa$ |
| VII | $CH_3-\overset{\overset{\displaystyle OH}{|}}{C}H-CH_3$ | $\overset{\displaystyle CH_3}{\underset{\displaystyle CH_3}{HC}}-O-\overset{\overset{\displaystyle COOCH_2CH_3}{|}}{\underset{\underset{\displaystyle COOCH_2CH_3}{|}}{C}}-O-CH_2-COOCH_2CH_3$ | $\overset{\displaystyle CH_3}{\underset{\displaystyle CH_3}{HC}}-O-\overset{\overset{\displaystyle COONa}{|}}{\underset{\underset{\displaystyle COONa}{|}}{C}}-O-CH_2-COONa$ |
| VIII | $CH_3CH_2CHCH_2CH_3$ with OH | analogous triester | analogous trisodium salt |
| IX | $CH_3(CH_2)_9CHCH_3$ with OH | analogous triester | analogous trisodium salt |
| X | $CH_3(CH_2)_3CHCH_2OH$ with CH₂CH₃ branch | analogous triester | analogous trisodium salt |
| XI | $CH_3(CH_2)_5CHCH_2-CH-CH_2OH$ with (CH₂)₃CH₃ branch | analogous triester | analogous trisodium salt |
| XII | $CH_3-\overset{\overset{\displaystyle CH_3}{|}}{\underset{\underset{\displaystyle CH_3}{|}}{C}}-CH_2OH$ | analogous triester | analogous trisodium salt |
| XIII | $CH_3-CH-CH_3$ / $CH_2$ / $HC-OH$ / $CH_2$ / $CH_3CH-CH_3$ | analogous triester | analogous trisodium salt |

TABLE I-continued

| Example | Hydroxy Containing Compound | Ester Product (5) | Salt Product (5) |
|---|---|---|---|
| XIV | CH₃-CH₂-HC(OH)-CH₂-CH(CH₃)-CH₃ (branched alcohol) | Ethyl ester tetracarboxylate with branched alkyl ether | Sodium salt tetracarboxylate with branched alkyl ether |
| XV | cyclohexanol | cyclohexyl ether of tetra(ethoxycarbonyl) methane | cyclohexyl ether of tetra(sodium carboxylate) methane |
| XVI | cyclopentanol | cyclopentyl ether of tetra(ethoxycarbonyl) methane | cyclopentyl ether of tetra(sodium carboxylate) methane |
| XVII | 3-methylcyclopentanol | 3-methylcyclopentyl ether of tetra(ethoxycarbonyl) methane | 3-methylcyclopentyl ether of tetra(sodium carboxylate) methane |
| XVIII | 3,3-dimethylcyclopentanol | 3,3-dimethylcyclopentyl ether of tetra(ethoxycarbonyl) methane | 3,3-dimethylcyclopentyl ether of tetra(sodium carboxylate) methane |
| XIX | 3-methylcyclohexanol | 3-methylcyclohexyl ether of tetra(ethoxycarbonyl) methane | 3-methylcyclohexyl ether of tetra(sodium carboxylate) methane |
| XX | 3-ethyl-5-methylcyclohexanol | 3-ethyl-5-methylcyclohexyl ether of tetra(ethoxycarbonyl) methane | 3-ethyl-5-methylcyclohexyl ether of tetra(sodium carboxylate) methane |

TABLE I-continued

| Example | Hydroxy Containing Compound | Ester Product (5) | Salt Product (5) |
|---|---|---|---|
| XXI | 3-methylphenol | triethyl ester derivative | trisodium salt derivative |
| XXII | 4-dodecylphenol | triethyl ester derivative | trisodium salt derivative |
| XXIII | 4-(2-ethylhexyl... variant)phenol | triethyl ester derivative | trisodium salt derivative |
| XXIV | 3-methyl-5-ethylphenol | triethyl ester derivative | trisodium salt derivative |
| XXV | 2-methylphenol (with $C_2H_5$) | triethyl ester derivative | trisodium salt derivative |
| XXVI | 3-chlorophenol | triethyl ester derivative | trisodium salt derivative |
| XXVII | 3-nitrophenol | triethyl ester derivative | trisodium salt derivative |

TABLE I-continued

| Example | Hydroxy Containing Compound | Ester Product (5) | Salt Product (5) |
|---|---|---|---|
| XXVIII | 3-chloro-5-nitrophenol | triethyl ester of 3-chloro-5-nitrophenoxy orthocarbonate | trisodium salt of 3-chloro-5-nitrophenoxy orthocarboxylate |
| XXIX | 2-methyl-4-chlorophenol | triethyl ester of 2-methyl-4-chlorophenoxy orthocarbonate | trisodium salt of 2-methyl-4-chlorophenoxy orthocarboxylate |
| XXX | 4-acetamidophenol | triethyl ester | trisodium salt |
| XXXI | 4-methoxyphenol | triethyl ester | trisodium salt |
| XXXII | CH₃OCH₂CH₂OH | triethyl ester | trisodium salt |
| XXXIII | (CH₃)₂CHO(CH₂CH₂O)₃CH₂CH₂OH | triethyl ester | trisodium salt |
| XXXIV | CH₃O(CH₂CHO(CH₃))₃CH₂CHOH | triethyl ester | trisodium salt |
| XXXV | phenoxy triethyleneglycol | triethyl ester | trisodium salt |
| XXXVI | HOCH₂CH₂OCH₂CH₂OCH₂CH₂OH | triethyl ester | trisodium salt |

*(Table contains complex chemical structural formulas which cannot be fully rendered in markdown. The Hydroxy Containing Compounds in column 2 react to form the corresponding Ester Products (triethyl esters, with COOCH₂CH₃ groups) in column 3 and Salt Products (trisodium salts, with COONa groups) in column 4, all based on an orthocarbonate/orthocarboxylate core structure: R—O—C(—CH₂—O—)(—COOR')₂ with —CH₂—COOR' substituents.)*

TABLE I-continued

| Example | Hydroxy Containing Compound | Ester Product (5) | Salt Product (5) |
|---|---|---|---|

XXXVII: $CH_3(CH_2)_4CH(CH_2)_3CH_2OH$

Ester Product: 
$$COOC_2H_5\ COOC_2H_5\ \ \ \ COOC_2H_5$$
$$H_2C-O-C-O-(CH_2CH_2O)_2CH_2CH_2O-C-O-CH_2$$
$$COOC_2H_5\ \ \ \ \ \ \ \ \ \ \ \ \ \ \ \ \ \ \ \ \ \ \ \ \ \ \ \ \ COOC_2H_5$$
and
$$CH_3(CH_2)_4CH(CH_2)_3CH_2-O-C-O-CH_2$$
with $COOC_2H_5$ groups Salt Product:
$$COONa\ COONa\ \ \ \ COONa$$
$$C-CH_2-O-C-O-(CH_2CH_2O)_2CH_2CH_2-O-C-O-CH_2$$
$$COONa\ \ \ \ \ \ \ \ \ \ \ \ \ \ \ \ \ \ \ \ \ \ \ \ \ \ \ \ \ \ \ \ \ COONa$$
and
$$CH_3(CH_2)_4CH(CH_2)_3CH_2-O-C-O-CH_2$$
with $COONa$ groups

XXXVIII: $C_6H_5CH_2OH$ (benzyl alcohol)

Ester Product: $C_6H_5CH_2O-C(COOC_2H_5)_2-O-CH_2(COOC_2H_5)_2$
Salt Product: $C_6H_5CH_2O-C(COONa)_2-O-CH_2(COONa)_2$

XXXIX: $CH_3(CH_2)_7CH=CH(CH_2)_7CH_2OH$

Ester Product: $H(CH_2)_7CH=CH(CH_2)_8-O-C(COOC_2H_5)_2-O-CH_2(COOC_2H_5)_2$
Salt Product: $H(CH_2)_7CH=CH(CH_2)_8-O-C(COONa)_2-O-CH_2(COONa)_2$

XL: $H(CH_2)_5CH=CHCH_2CH=CH(CH_2)_8OH$

Ester Product: $H(CH_2)_5CH=CHCH_2CH=CH(CH_2)_8-O-C(COOC_2H_5)_2-O-CH_2(COOC_2H_5)_2$
Salt Product: $H(CH_2)_5CH=CHCH_2CH=CH(CH_2)_8-O-C(COONa)_2-O-CH_2(COONa)_2$

XLI: $H(CH_2)_8C\equiv C(CH_2)_8OH$

Ester Product: $H(CH_2)_8C\equiv C(CH_2)_8-O-C(COOC_2H_5)_2-O-CH_2(COOC_2H_5)_2$
Salt Product: $H(CH_2)_8C\equiv C(CH_2)_8-O-C(COONa)_2-O-CH_2(COONa)_2$

XLII: 4-dodecylbenzyl alcohol, $CH_3(CH_2)_{11}-C_6H_4-CH_2OH$

Ester Product: $CH_3(CH_2)_{11}-C_6H_4-CH_2-O-C(CO_2C_2H_5)_2-O-CH_2CO_2C_2H_5$
Salt Product: $CH_3(CH_2)_{11}-C_6H_4-CH_2-O-C(CO_2Na)_2-O-CH_2CO_2Na$

XLIII: 4-phenylphenol (4-hydroxybiphenyl)

Ester Product: $(C_6H_5)-C_6H_4-O-C(COOC_2H_5)_2-O-CH_2(COOC_2H_5)_2$
Salt Product: $(C_6H_5)-C_6H_4-O-C(COONa)_2-O-CH_2(COONa)_2$ TABLE I-continued

| Example | Hydroxy Containing Compound | Ester Product (5) | Salt Product (5) |
|---|---|---|---|
| XLIV | 2-naphthol | naphthyl-O-C(COOC$_2$H$_5$)(CH$_2$COOC$_2$H$_5$)(COOC$_2$H$_5$) | naphthyl-O-C(COONa)(CH$_2$COONa)(COONa) |
| XLV | HO(CH$_2$)$_5$OH | HO(CH$_2$)$_5$O-C(COOC$_2$H$_5$)(CH$_2$COOC$_2$H$_5$)(COOC$_2$H$_5$) and CH$_2$(COOC$_2$H$_5$)-CH$_2$-O-C(COOC$_2$H$_5$)(CH$_2$COOC$_2$H$_5$)(COOC$_2$H$_5$) type bis-ester | HO(CH$_2$)$_5$O-C(COONa)(CH$_2$COONa)(COONa) and bis-salt |
| XLVI | HO(CH$_2$)$_{20}$OH | HO(CH$_2$)$_{20}$O-C(COOC$_2$H$_5$)(CH$_2$COOC$_2$H$_5$)(COOC$_2$H$_5$) and bis-ester | HO(CH$_2$)$_{20}$O-C(COONa)(CH$_2$COONa)(COONa) and bis-salt |
| XLVII | 1,4-cyclohexanediol | mono- and bis- cyclohexyl ester with COOC$_2$H$_5$ groups | mono- and bis- cyclohexyl salt with COONa groups |
| XLVIII | 1,3-cyclopentanediol | mono- and bis- cyclopentyl ester with COOC$_2$H$_5$ groups | mono- and bis- cyclopentyl salt with COONa groups |

–

EXAMPLE L

The product salts prepared according to Examples I through XLIX when tested for sequestration function using the procedures described by Matzner et al, "Organic Builder Salts as Replacements for Sodium Tripolyphosphate", Tenside Detergents, 10, Heft 3, pages 119–125 (1973), are found to be effective sequestrants.

EXAMPLE LI

Detergent formulations containing 50% of the builder shown in Table 2 below; 17% linear alkylbenzene sulfonate having an average molecular weight of about 230; 6% sodium silicate; remainder, sodium sulfate are prepared. The formulations are tested by washing identically soiled fabric swatches (indicated in the Table) in water of 200 ppm hardness at 49° C. containing 0.15% detergent formulation using identical washing techniques. The reflectivity of the soiled swatches before and after washing is measured instrumentally and the difference reported in Table 2 as $\Delta Rd$. High $\Delta Rd$ values are indicative of correspondingly high detergency effectiveness.

Table 2

| Builder | Cotton Fabric $\Delta Rd$ | Polyester/ Cotton Fabric $\Delta Rd$ |
|---|---|---|
| none (a filler-sodium sulfate-is used in place of builder) | <13 | <5 |
| $CH_3CH_2-O-\underset{\underset{COONa}{\|}}{\overset{\overset{COONa}{\|}}{C}}-O-CH_2\text{(COONa)}$ | 16.9 | 8.3 |
| $CH_3-O-\underset{\underset{COONa}{\|}}{\overset{\overset{COONa}{\|}}{C}}-O-CH_2\text{(COONa)}$ | 14.6 | 8.0 |
| $C_{12}H_{25}-O-\underset{\underset{COONa}{\|}}{\overset{\overset{COONa}{\|}}{C}}-O-CH_2\text{(COONa)}$ | 14.4 | 6.4 |
| $\left(CH_2-O-\underset{\underset{COONa}{\|}}{\overset{\overset{COONa}{\|}}{C}}-O-(CH_2)_2\right)_2-O$ (COONa) | 15.2 | 8.9 |

The data presented in Table 2 show the salt forms of the compounds of this invention to be effective detergency builders.

EXAMPLE LII

Aqueous solutions of the salt products prepared according to Examples I through XLIX are reacted with hydrochloric acid to yield the corresponding acid forms. Reaction of the acids with ammonium hydroxide yields the corresponding ammonium salts which are found to be effective sequestrants when tested according to the procedure referred in Example L.

What is claimed is:

1. A machine dishwashing composition comprising (a) from 5 to 90 percent by weight of a compound corresponding to the formula

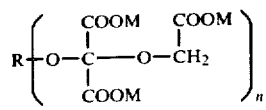

wherein M is alkali metal or ammonium and wherein n is a number from 1 through 3, and wherein R is selected from an alkyl radical having from 1 to 20 carbon atoms, an alkenyl radical having from 1 to 20 carbon atoms, an alkynyl radical having from 1 to 20 carbon atoms, a cycloalkane radical having from 3 to 20 carbon atoms, an alkanol radical having from 2 to 20 carbon atoms, an ether radical having at least 3 carbon atoms, an aryl radical having at least 6 carbon atoms, a substituted aryl radical having at least 6 carbon atoms wherein the substituents are halogen, nitro, amide or carboxyalkyl substituents, aralkyl radicals having at least 7 carbon atoms and arylether radicals having at least 7 carbon atoms, and (b) from 0 to 5 percent by weight of a surfactant selected from the group consisting of low-foaming anionic and nonionic surfactants and mixtures thereof, (c) a chlorine-providing material selected from the group consisting of potassium dichlorocyanurate; sodium dichlorocyanurate; [(monotrichloro)tetra-(monopotassium dichloro)] penta-isocyanurate; (monotrichloro) (monopotassium dichloro) diisocyanurate; chlorinated trisodium phosphate, said chlorine-providing material being present in an amount sufficient to provide from 0.5% to 2% by weight available chlorine, and (d) from 5% to 30% by weight soluble sodium silicate having an $SiO_2$ to $Na_2O$ mole ratio of from 1:1 to 3.2:1.

2. The formulation of claim 1 wherein said substituent is attached to an uncarboxylated carbon atom.

3. The formulation of claim 1 wherein said substituents constitute at least 50% of the weight of said compound.

4. The formulation of claim 1 wherein said substituents constitute at least 85% of the weight of said compound.

5. The formulation of claim 1 wherein component (a) is a compound represented by the formula

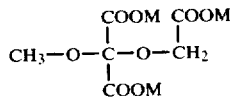

6. The formulation of claim 1 wherein component (a) is a compound represented by the formula

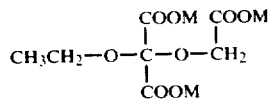

* * * * *